United States Patent
Karjalainen et al.

(10) Patent No.: US 9,526,472 B2
(45) Date of Patent: Dec. 27, 2016

(54) METHOD AND ARRANGEMENT FOR ESTIMATING MINERAL DENSITY OF A BONE

(75) Inventors: Janne Karjalainen, Leppäkaarre (FI); Ossi Riekkinen, Vuorela (FI)

(73) Assignee: BONE INDEX FINLAND OY, Kuopio (FI)

( * ) Notice: Subject to any disclaimer, the term of this patent is extended or adjusted under 35 U.S.C. 154(b) by 238 days.

(21) Appl. No.: 13/821,883

(22) PCT Filed: Sep. 9, 2011

(86) PCT No.: PCT/FI2011/050772
§ 371 (c)(1),
(2), (4) Date: May 20, 2013

(87) PCT Pub. No.: WO2012/032225
PCT Pub. Date: Mar. 15, 2012

(65) Prior Publication Data
US 2013/0245443 A1 Sep. 19, 2013

(30) Foreign Application Priority Data

Sep. 9, 2010 (FI) .................................. 20105936

(51) Int. Cl.
*A61B 8/08* (2006.01)
*A61B 6/00* (2006.01)

(52) U.S. Cl.
CPC ........... *A61B 8/0875* (2013.01); *A61B 8/5223* (2013.01); *A61B 8/5292* (2013.01); *A61B 6/505* (2013.01); *A61B 8/0858* (2013.01)

(58) Field of Classification Search
CPC .............................. A61B 8/0875; A61B 1/00
See application file for complete search history.

(56) References Cited

U.S. PATENT DOCUMENTS 4,941,474 A * 7/1990 Pratt, Jr. ................. 600/437
5,218,963 A * 6/1993 Mazess ................... 600/449
(Continued)

FOREIGN PATENT DOCUMENTS

CN 1596084 A 3/2005
EP 1393680 A1 3/2004
(Continued)

OTHER PUBLICATIONS

C. Ohlsson, A. Daelid, M. Nilsson, J. Melin, D. Mellstrom, and M. Lorentzon, "Cortical Consolidation due to Increased Mineralization and Endosteal Contraction in Young Adult Men: A Five-Year Longitudinal Study", J. Clin. Endocrinol Metlb, 96(7), 2011.*
(Continued)

*Primary Examiner* — Tse Chen
*Assistant Examiner* — Joanne Hoffman
(74) *Attorney, Agent, or Firm* — Berggren Inc.

(57) ABSTRACT

An arrangement is adapted to determine an estimate for mineral density related to a patient's first bone, wherein said first bone is associated with a femoral head, neck and/or a lumbar spine. The estimate determined by determining a first parameter, which is related to a property change in a measurement signal, most preferably an ultrasonic signal, launched towards some second bone of said patient other than the first bone after the measurement signal has been in interaction with said second bone. This is followed by determining an estimate for mineral density related to said patient's first bone by using said first parameter.

12 Claims, 2 Drawing Sheets

(56) References Cited

U.S. PATENT DOCUMENTS

| | | | |
|---|---|---|---|
| 5,817,020 A * | 10/1998 | Ishii et al. ............... | 600/437 |
| 5,840,029 A * | 11/1998 | Mazess et al. ............ | 600/437 |
| 6,213,934 B1 * | 4/2001 | Bianco ............... | A61B 5/053 |
| | | | 600/14 |
| 6,468,215 B1 * | 10/2002 | Sarvazyan et al. ........ | 600/438 |
| 6,589,178 B2 * | 7/2003 | Sakai ................ | A61B 5/053 |
| | | | 600/442 |
| 8,880,143 B2 * | 11/2014 | Kalvesten ........... | G06T 7/0014 |
| | | | 378/54 |
| 2002/0006181 A1 | 1/2002 | MacKenzie et al. | |
| 2002/0156378 A1 | 10/2002 | Sakai | |
| 2003/0223537 A1 | 12/2003 | Puzas | |
| 2005/0004457 A1 | 1/2005 | Moilanan et al. | |
| 2005/0015002 A1 * | 1/2005 | Dixon et al. ............... | 600/407 |
| 2005/0197576 A1 * | 9/2005 | Luo ................ | A61B 8/0875 |
| | | | 600/438 |
| 2006/0062442 A1 * | 3/2006 | Arnaud ............... | A61B 6/505 |
| | | | 382/128 |
| 2009/0143681 A1 * | 6/2009 | Jurvelin et al. ........... | 600/449 |
| 2010/0185086 A1 | 7/2010 | Suetoshi et al. | |

FOREIGN PATENT DOCUMENTS

| | | |
|---|---|---|
| JP | 2002-238904 | 8/2002 |
| WO | WO 01/73116 A2 | 10/2001 |
| WO | WO 2008/146513 A1 | 12/2008 |
| WO | WO 2010/093769 A2 | 8/2010 |

OTHER PUBLICATIONS

Padilla, F., Jenson, F., Boussson, V., Peyrin, F., and Laugier, P., "Relationships of trabecular bone structure with quantitative ultrasound parameters: In vitro study on human proximal femur using transmission and backscatter measurements", Bone 42, pp. 1193-1202, 2008.*

Anne C. Looker, Thomas J. Beck, and Eric S. Orwoll, "Does Body Size Account for Gender Differences in Femur Bone Density and Geometry?", Journal of Bone and Mineral Research, vol. 16, 2001.*

Moilanen, P., Nicholson, N., Kilappa, V., Cheng, S., Timonen, J., "Assessment of the Cortical Bone Thickness Using Ultrasonic Guided Waves: Modelling and In Vitro Study", Ultrasound in Med. & Biol., vol. 33, No. 2, pp. 254-262, 2007.*

Zagzebski, J., Rossman, P. Mesina, C., Mazess, R., Madsen, E., "Ultrasound Transmission MEasurements THrough the Os Calcis", Calcif Tissue Int, vol. 49, pp. 107-111, 1991.*

Japanese Office Action (English and Japanese versions) for Japanese Application No. 2013-527654, dated Aug. 5, 2015, 6 pages.

Two pages from Russian book entitled "Sistemnyj osteoporoz" and English language machine translation of the two pages, 2000.

* cited by examiner

METHOD AND ARRANGEMENT FOR ESTIMATING MINERAL DENSITY OF A BONE

PRIORITY CLAIM

This application is a National Phase entry of PCT Application No. PCT/FI2011/050772, filed Sep. 9, 2011, which claims priority from Finland Application No. 20105936, filed Sep. 9, 2010, the disclosures of which are hereby incorporated by referenced herein in their entirety.

FIELD OF THE INVENTION

The present invention relates to a method and arrangement for the assessment of mineral density related to a patient's bone, such as the femoral head, neck and/or the lumbar spine.

BACKGROUND OF THE INVENTION

Musculoskeletal disorders (MSDs) are the leading cause of morbidity and the most common source of chronic long-term pain and disability all over the world. Osteoporosis or bone loss disease is an explosively increasing national MSD. Some predictions indicate a further increase in fracture numbers, resulting in higher-than-before costs for society. A majority of the osteoporotic patients are not identified until after several low-energy bone fractures. The prior art discloses a few methods of diagnosing bone mineral density or osteoporosis, such as, for example, central dual-energy X-ray absorptiometry (DXA), which is a so-called gold standard in osteoporosis diagnostics. In clinical sense, this meauring technique enables a diagnosis of osteoporosis from determined bone mineral density values (BMD) in the femoral neck or lumbar spine. In practice, the determination is performed by comparing the result determined from a patient with the normal values of young women. If the determined result is 1-2.5 normal distributions below average, the patient has osteopenia. If the result is more than 2.5 normal distributions below average, the patient is diagnosed for osteoporosis.

However, the prior art solutions involve some problems. First of all, there is a quite limited supply of X-ray equipment suitable for such a determination, and secondly, the equipment is expensive (typically in the order of about 50 000 to 100 000 €, thus not applicable in general healthcare). In addition, the equipment is bulky and requires a room of its own and, because of X-radiation, the measurements conducted thereby always produce a radiation dose for the patient and, especially when measuring an upper segment of the femur, the radiation dose is applied to the close proximity of sensitive internal organs and genital cells. The use of X-ray technology also requires that an operator of the apparatus be familiar with and trained for operating an ionizing radiation source, as well as increases a radiation dose received by the operator. Therefore, the use of a DXA method for the extensive screening of risk groups for osteoporosis on general healthcare level is challenging and, in some cases, even impossible.

The prior art also discloses DXA (pDXA, peripheral DXA) and ultrasonic techniques useful for measuring extremities (for example the heel), which are potential methods for general healthcare level. However, the prognosis provided by such equipment regarding for example density in the upper femur segment is nevertheless poor or at best moderate (r=0.2-0.6) and, hence, the techniques cannot be used very reliably in osteoporosis diagnostics (current care guideline). Indeed, it has been estimated that approximately 40 to 60% of the patients measured with these available techniques must be dispatched to central DXA examination for confirming the diagnosis of osteoporosis.

SUMMARY OF THE INVENTION

One objective of the present invention is to eliminate some of the drawbacks associated with the prior art. According to one embodiment, the present invention seeks to improve the prognosis of mineral density related to the femoral head, neck and/or the lumbar spine and, at the same time, to eliminate or minimize a radiation dose applied to the patient. A further objective of the present invention is to produce a parameter or estimate that would enable predicting a patient's bone fracture probability.

Some objectives of the present invention are achieved by a method for an assessment of mineral density related to a patient's first bone, wherein said first bone is associated with a femoral head, a femoral neck and/or a lumbar spine, characterized in that the method comprises determining with a pulse echo method a first parameter, which is related to a property change in an ultrasonic measurement signal launched towards the cortical bone of said patient's tubular bone after the measurement signal has been in interaction with the cortical bone of said tubular bone, wherein said cortical bone of a tubular bone is some second bone other than said first bone, and determining an estimate for mineral density related to said patient's first bone by using said first parameter.

In addition, the present invention is directed to an arrangement for an assessment of mineral density related to a patient's first bone, wherein said first bone is associated with a femoral head, a femoral neck and/or a lumbar spine, characterized in that the arrangement is adapted to transmit with a pulse echo method an ultrasonic measurement signal towards the cortical bone of a patient's tubular bone, as well as to receive said ultrasonic measurement signal after its interaction with a tubular bone's cortical bone, wherein said tubular bone's cortical bone is some second bone other than said first bone, to determine a first parameter, which is related to a property change in said ultrasonic measurement signal after the measurement signal has been in interaction with said tubular bone's cortical bone, and to determine an estimate for mineral density related to said patient's first bone by using said first parameter. The present invention is also directed to a computer program product for an assessment of mineral density related to a patient's first bone, wherein said first bone is associated with a femoral head, a femoral neck and/or a lumbar spine, characterized in that the computer program product is adapted to determine with a pulse echo method a first parameter, which is related to a property change in an ultrasonic measurement signal launched towards the cortical bone of said patient's tubular bone after the measurement signal has been in interaction with said tubular bone's cortical bone, wherein said cortical bone of a tubular bone is some second bone other than said first bone, and to determine an estimate for mineral density related to said patient's first bone by using said first parameter, as said computer program product is run with a data processing processor.

The present invention involves determining an estimate for the mineral density related to a first bone of the patient, wherein said first bone is associated particularly with the femoral head, neck and/or the lumbar spine. According to one embodiment, in order to determine an estimate for the first bone mineral density, an ultrasonic pulse-echo method is used for determining a first parameter, which relates to a property change in an ultrasonic measurement signal launched towards a second bone other than the first bone after the measurement signal has been in interaction with said second bone. The second bone can be for example the calcaneus, tibia, finger, radius and/or ulna, and especially the cortical bone of a tubular bone connected. These are considerably easier and more accurate to measure than for example the femoral head region, because the femoral head region has typically a target of measurement covered by soft tissues, which interfere with the measurement and have a propensity for giving false results. In addition, the femoral head has a geometry that sets up challenges for the measurement.

According to one embodiment of the present invention, the applied measurement signal is an ultrasonic signal, which is launched for example with any ultrasonic transmitter known from the prior art. Most preferably, the method is an ultrasonic pulse-echo method. According to a second embodiment, the measurement signal launched towards a second bone may comprise X-radiation. It should be noted, however, that, even if the applied radiation were to consist of per se ionizing X-radiation, the fact is that, as it is launched towards some above-mentioned second bone, the harmful radiation dose received by a patient shall not be very significant since these regions do not feature anatomically sensitive organs as opposed, for example, to the femoral head region. However, the method, specifically based on an ultrasonic method alone, provides a remarkable benefit in terms of not exposing the patient to a harmful dose of radiation. Furthermore, the ultrasound-based installations present attractive price and compact size for example with respect to X-ray equipment.

Said property change of a measurement signal is preferably associated for example with the attenuation or penetration of X-radiation, or more preferably with the attenuation, velocity change, penetration, reflection, and/or scatter of ultrasound, while the measurement signal is in interaction with said second bone. In a particularly beneficial case, said property change of a measurement signal is the reflection of ultrasound from the first and second edges of a tubular bone's cortical bone, enabling for example the thickness of said cortical bone to be determined. The property change can also be a time lapse detected when the measurement signal is in interaction with said second bone as opposed to a condition in which the measurement signal is not in interaction with the second bone. According to one embodiment of the present invention, said property changes of a measurement signal enable determining for example the thickness of an entire bone, such as for example the calcaneus thickness, or for example the cortical layer thickness of ulna, radius or tibia. It should be noted that for example the thickness of cortical bone in tibia provides only a fairly rough prediction regarding for example the femoral neck bone mineral density in comparison with the femoral neck bone mineral density determined for example by DXA technology.

In osteoporosis, the cortical layer thickness diminishes, so just the measurement of thickness in itself possesses diagnostic value. In penetration measurement, when measuring for example from the heel, the properties of both trabecular bone and cortical bone have an impact on the measured signal, making the traditional penetration measurement unfavorable. Changes in the properties (composition/structure) of various bone components (trabecular bone/cortical bone) may further lead in through-transmission measurements to opposite changes in the measurement signal. Still furthermore, the composition of bone marrow (yellow/red) has an independent impact on the measurement signal. However, these mentioned problems can be resolved with an ultrasonic pulse-echo measuring method of the present invention.

It should also be noted that the penetration measurement requires at least two sensors while the tubular bone measurement can be conducted by using just one sensor. This also makes it possible to measure several parts of the skeletal system more easily, because the use of a single sensor in parts of varying anatomy is remarkably simple as opposed, for example, to the use of two sensors which must always be positioned at a certain minimum distance from each other and/or at a certain angle relative to each other. The penetration measurement is inevitably affected also by a soft tissue layer present on top of the bone, whereas, in the tubular bone thickness measurement, the thickness/composition of a soft tissue layer has no impact. Therefore, the method of the present invention is considerably more accurate and simpler to carry out than methods based on penetration measurements.

According to one preferred embodiment of the present invention, in order to determine a mineral density estimate, there is also determined a set of second parameters, wherein said set of second parameters comprises for example the age and weight of a particular patient. The patient's age and weight as such are rather weak or moderate predictors regarding the mineral densities of targets associated with the femoral head, but, in connection with one embodiment, it has now been discovered that the combination of certain parameters provides a high-quality correlation for the mineral density of targets (for example the neck) connected with the femoral head. According to one exemplary embodiment of the present invention, such parameters comprise at least as follows:

a parameter related to a property change in a measurement signal after the measurement signal has been in interaction with said second bone, or related to some other parameter derived therefrom, such as cortical bone thickness, and the patient's age and weight or another similar second parameter.

According to one embodiment of the present invention, the estimate for mineral density regarding said patient's first bone is indeed determined by using said first parameter, but according to one other embodiment, the estimate is worked out by additionally using also at least one of the second parameters presented in this document.

In Particular, according to one embodiment of the present invention, said first parameter relates to the thickness of cortical bone as measured from one or more points thereof, for example from the head, mid-section, and/or bottom. Most preferably, the cortical bone thickness is determined by using ultrasound technology. According to one other embodiment, the thickness of cortical bone can also be determined by means of a method based on X-ray technology.

According to one embodiment of the present invention, the determination of a mineral density estimate is conducted by additionally using a set of second parameters, which comprises at least one of the following: the patient's age, weight, height, body mass index, hormonal status (like how many years since menopause, estrogen level), femoral geometric parameter (for example cross-sectional area or diameter) as measured from at least one point, for example from the femoral shaft and/or neck, and the patient's hand grip strength. According to one embodiment, the second parameter may comprise (either in addition to those mentioned above or by itself) a property change in an ultrasonic signal launched towards said first bone after said ultrasonic signal has been in interaction with said first bone, such as for example an AIB parameter (dB) (Apparent Integrated Backscatter) determined from the backscatter of ultrasound from the femoral head and/or neck. Namely, it has now been discovered by the inventors that any parameter among said set of second parameters by itself is only moderately capable of predicting the mineral density of a bone associated with the femoral head region, but, when these parameters with a poor or moderate capability of predicting the mineral density of targets in the femoral head region are combined with the above-mentioned first and/or second parameters, the result is most preferably a very strong prognosis for the mineral density of femoral head region bones.

It should be noted that the composition and amount of soft tissue may cause an error of even more than 100% in the pulse echo measurement of a soft tissue-bone combination in the process of measuring the strength (dB) of ultrasonic backscatter from the femoral head and/or neck (obtaining a so-called AIB parameter [dB]). According to one embodiment, the effect of soft tissue on the measurement can be corrected for example by DFUS technique (Dual Frequency Ultrasound, a multi-frequency measurement for example with frequencies 2.25 MHz and 5.0 MHz) and/or by accounting for attenuation occurring in the cortical bone layer. The attenuation of ultrasound in fat and muscle tissue is a frequency-dependent property, whereby these two reflection coefficients (determined from bone surface at two different frequencies) and a time signal can be used for calculating the amounts of fat and muscle from the soft tissue on top of the bone and for determining thereby the total soft tissue thickness. The effect of a soft tissue can be determined for example when the properties of an ultrasonic signal reflected or scattered from bone are compared to the properties of a signal reflected for example from a water-metal interface.

According to one preferred embodiment of the present invention, the mineral density estimate is worked out by combining the foregoing parameters (at least a first parameter and at least one parameter from the set of second parameters), for example by means of a regression analysis, such as by means of linear regression.

In addition, according to one embodiment, a parameter representing the degree of a patient's osteoporosis can be determined by using a mineral density estimated related to the patient's first bone and by comparing said mineral density estimate to reference values regarded as normal. For example, in case the determined result is 1-2.5 normal distributions below average, the patient has osteopenia, and in case the result is more than 2.5 normal distributions below average, the patient is diagnosed for osteoporosis.

The present invention offers distinct benefits over what has been described above. For example, the assessment of mineral density and a subsequent osteoporosis diagnosis can be conducted in public health clinics with no need to send the patient to central hospitals. In addition, since all patients visiting health clinics and included in a risk group for osteoporosis can be tested, it is also possible to start medication with patients who require it and thereby to impede or at least slow down the advancement of osteoporosis. Thus, the costs resulting from bone fractures can also be minimized. Still further, the present invention enables minimizing the dose of ionizing radiation applied to a patient and concentrating it in regions with no sensitive internal organs or genital cells. In addition, by using a parameter indicating the femoral neck mineral density predicted by the present invention for example in a fracture probability assessing calculation program, it is possible to determine the bone fracture probability for a patient for example for the next 10 years with the use of measuring techniques appropriate for general health care, yet in a sufficiently reliable manner and at low costs, and moreover to start a possible pre-emptive activity or therapy.

BRIEF DESCRIPTION OF THE FIGURES

Preferred embodiments of the present invention will be described in slightly more detail in the next section with reference to the accompanying figures, in which.

DETAILED DESCRIPTION OF THE FIGURES

Figure 1:
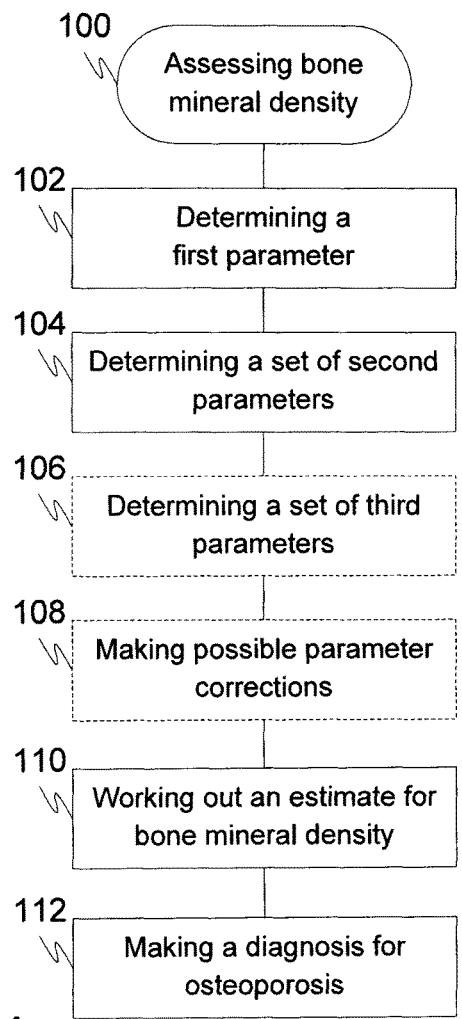
FIG. 1 shows one exemplary method for the assessment of bone mineral density acording to one preferred embodiment of the present invention.

Referring now generally to the figures, FIG. 1 shows one exemplary method 100 for the assessment of a patient's first bone density according to one preferred embodiment of the present invention, wherein the first bone is associated for example with the femoral head, neck and/or the lumbar spine. Step 102 comprises determining a first parameter, which is related to a property change in a measurement signal launched towards a second bone of the patient other than the first bone after the measurement signal has been in interaction with said second bone. Said first parameter may represent for example the magnitude of a property change in the measurement signal, such as for example the rate of ultrasound attenuation, the rate of velocity change, or the strength of reflection or scatter or the strength of intensity change, or the time gap between signals reflected from bone, particularly the time gap between signals reflected from first and second bone surfaces in the direction of a measurement signal. The first parameter may also be a new quantity determined by means of the measured properties of a measurement signal, such as for example the second bone thickness or the ulnar/radius or tibial cortical bone thickness as measured from one or more points.

Step 104 comprises determining a set of second parameters, such as for example a patient's age and weight or some other second parameter presented in this document.

Step 106 may additionally comprise determining more precisely the set of second parameters, comprising at least one of the following: the patient's age, weight, body mass index, femoral geometric parameter (for example cross-sectional area or diameter) for example from the femoral shaft and/or neck, and the patient's hand grip strength. According to one embodiment, the set of second parameters may comprise (either in addition to those mentioned above or by itself) a property change in an ultrasonic signal launched towards said first bone after said ultrasonic signal has been in interaction with said first bone, such as for example an AIB parameter (dB) determined from the backscatter of ultrasound from the femoral head and/or neck. It should be noted, however, that step 106 is optional. Furthermore, step 108 may comprise conducting possible parameter corrections, such as for example a correction of the ultrasonic signal property change or a DFUS correction regarding a measurement of the ultrasonic backscatter strength (dB) as measured from the femoral head and/or neck. The parameter corrections may be related to errors caused for example by the composition or amount of soft tissue. Step 108 is also optional.

Step 110 comprises working out an estimate for the mineral density of a patient's first bone by combining the above-determined parameters (at least the first parameter and some of the set of second parameters). The combination can be conducted for example by means of regression, such as for example by means of linear regression (cf. FIGS. 2a and 2b)

The estimate for mineral density can be further used for determining a parameter representing the degree of a patient's osteoporosis, as well as a fracture risk predicting parameter (for example fracture probability) in step 112, for example by comparing said mineral density estimate to reference values regarded as normal.

According to one exemplary embodiment of the present invention, the thicknesses of cortical bone from lower and upper tibial segments ($CTh\_ds$ and $CTh\_pr$) and the ultrasound backscatter from femoral neck (AIB) were determined by pulse echo imaging (cf. table 1 below). The AIB was determined for 25 women and AIB was corrected by DFUS technique with the attenuation caused by soft tissue on top of the bone. Other parameters were determined for 29 women.

TABLE 1

|  | AIB (dB) | $CTh\_ds$ (mm) | $CTh\_pr$ (mm) | age (year) | weight (kg) | height (cm) | BMI (kg/m$^2$) |
| --- | --- | --- | --- | --- | --- | --- | --- |
| average | −51.2 | 3.12 | 2.15 | 74 | 68 | 161 | 26 |
| distribution | 5.6 | 0.68 | 0.56 | 3 | 13 | 6 | 5 |

In addition, as seen from table 2, the ultrasound backscatter (AIB) measured from femoral neck, the cortical bone thicknesses measured from tibia (from distal end $CTh\_ds$ and proximal end $CTh\_pr$), and initial information obtained about a patient (age, weight, body mass index (BMI)) are by themselves (linear correlation coefficientr) just poor or moderate predictors of the femoral neck bone mineral density (BMD).

TABLE 2

|  | AIB (dB) | $CTh\_ds$ (mm) | $CTh\_pr$ (mm) | age (year) | weight (kg) | height (cm) | BMI (kg/m$^2$) |
| --- | --- | --- | --- | --- | --- | --- | --- |
| BMD (g/cm$^2$) | −0.42* | 0.59** | 0.63** | −0.33 | 0.60** | 0.48** | 0.45* |

*$p < 0.05$, **$p < 0.01$

The parameters useful in at least one embodiment of the present invention can be processed for example with linear regression technique to provide a strong predictor for bone mineral density. The embodiment, which is conducted by using only cortical bone thicknesses, age, and weight, provides the following exemplary estimate for femoral neck mineral density ($r=0.87$, $n=29$, FIG. 2a):

$$BMD\_estimate\_1 = 0.912 - 0.014*age + 0.092*CTh\_ds + 0.006*weight + 0.098*CTh\_pr$$

The embodiment, which is conducted by using all determined parameters, provides the following exemplary mineral density estimate ($r=0.90$, $n=25$, FIG. 2b):

$$BMD\_estimate\_2 = 3.624 - 0.015*age + 0.070*CTh\_pr + 0.064*CTh\_ds - 0.061*BMI - 0.005*AIB - 0.016*height + 0.027*weight$$

It should be noted, however, that parameters of the above-presented estimates may have various coefficients in various embodiments, for example in accordance with the employed measurement material.

Figure 2A:
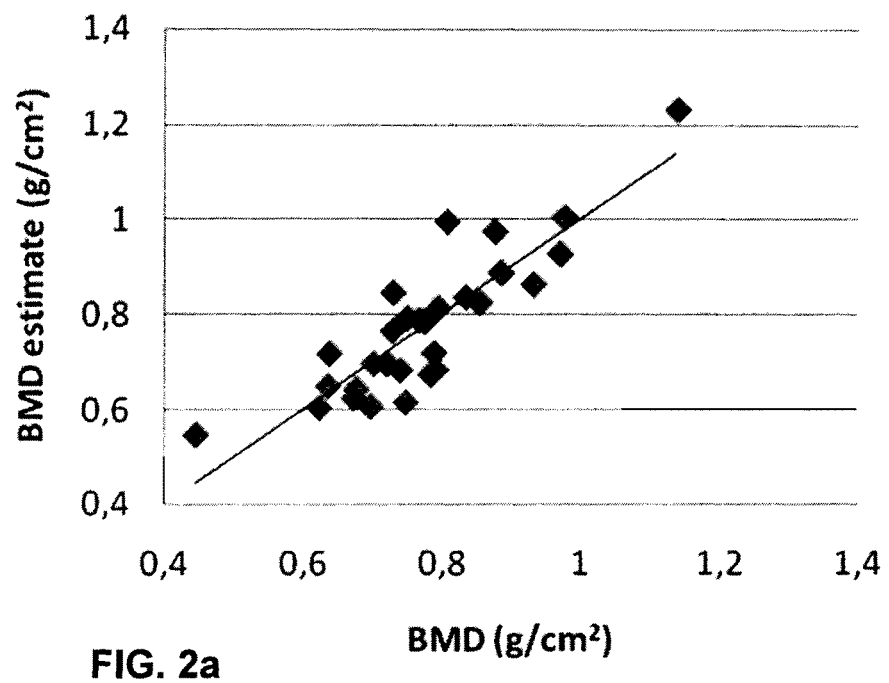
FIG. 2a shows the strength of prediction based on a patient's cortical bone thickness (distal and proximal end), age and weight for the patient's femoral neck mineral density as determined according to one embodiment of the present invention.
Figure 2B:
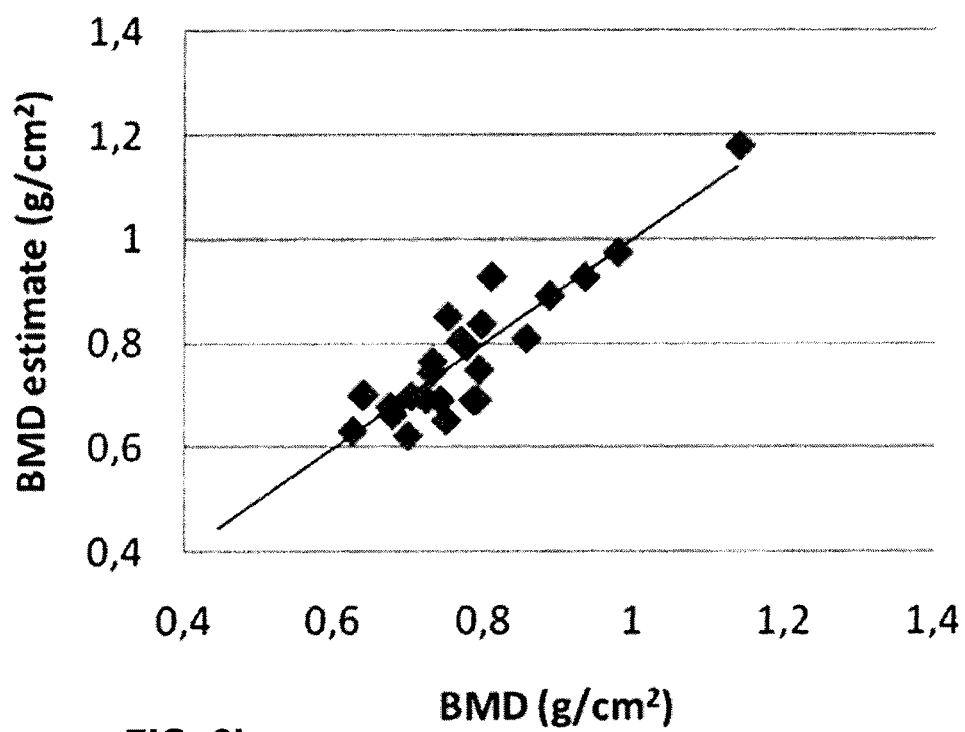
FIG. 2b shows the strength of prediction based on a combination of all determined parameters for the femoral neck mineral density as determined according to one embodiment of the present invention.

FIG. 2a illustrates the strength of a prediction, based on a patient's cortical bone thicknesses (distal and proximal end), age, and weight, for the patient's femoral neck mineral density ($r=0.87$, $n=29$), and FIG. 2b illustrates the strength of a prediction, based on the combination of all determined parameters (combined by linear regression technique), for femoral neck mineral density ($r=0.90$, $n=25$) as determined according to one embodiment of the invention.

Figure 3:
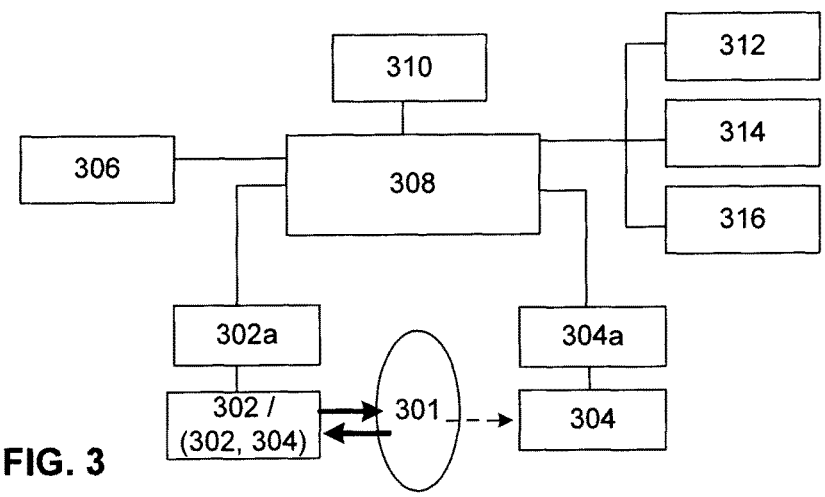
FIG. 3 shows one exemplary arrangement for the assessment of bone mineral density according to one preferred embodiment of the present invention.

FIG. 3 shows one exemplary arrangement 300 for the assessment of bone mineral density according to one preferred embodiment of the present invention, wherein the arrangement 300 comprises transmission means 302 for a measurement signal (especially pulse-echo measurement means for an ultrasound signal) for transmitting a measurement signal towards a patient's second bone 301 (other than the first bone), as well as reception means 304 for a measurement signal for receiving a measurement signal after its interaction with said second bone 301, preferably a reflected (such as reflected from cortical bone) ultrasound signal. The interacted signal can be for example an ultrasound signal and its property to be measured can be for example reflection, scatter (for example intensity or angle), velocity change, or attenuation. Alternatively, the interacted signal can be for example an X-ray beam and its property to be measured can be for example penetration or attenuation (dashed line in the figure).

It should be noted that, according to one embodiment, the reception means 304 can be located at various points in terms of measuring geometry. For example, in the process of determining a measurement signal after its passage through an object of measurement (for example in the process of measuring the attenuation of a measurement signal), the reception device 304 is preferably placed on the side of a measured object opposite to the transmission device 302. Respectively, in the process of measuring a measurement signal for reflection or backscatter from an object of measurement, the reception device 304 is preferably placed on the same side as the transmission device 302 with respect to the object of measurement. It should further be noted that, according to one embodiment of the present invention, the transmission device 302 may also be the reception device 304 at the same time, whereby the transmitter/receiver device 302/304 may comprise for example a physically common crystal, which first generates an ultrasound signal and then receives said ultrasound signal after its interaction with an object of measurement. It should be noted, in particular, that, in ultrasonic measuring technique, the pulse-echo measurement device comprises a single transceiver sensor (302/304), which is particularly handy in the process of measuring several different points.

The transmission and reception means 302, 304 may also involve some control electronics 302a, 304a therefor.

According to one embodiment, in particular, the control electronics are adapted to control the transmitter 302 and the receiver 304, such that the transmitter's transmission operation is discontinued for the duration of the receiver's reception operation in order to minimize interferences, especially in the embodiment using one and the same crystal to generate an ultrasound signal and to receive a signal reflected from an object. In addition, the arrangement preferably comprises elements 306 for feeding said second parameters into the arrangement, such as a keyboard or a graphical data entry tool. Moreover, at least some of said second parameters (the patient's height, body mass index, hormonal status, femoral geometric parameter (such as cross-sectional area or diameter) from the femoral shaft and/or neck, and the patient's hand grip strength) can be entered into the arrangement also by means of the elements 306. In addition, a parameter representing a property change in an ultrasound signal launched towards said first bone, after said ultrasound signal has been in interaction with said first bone, such as for example an AIB parameter (dB) determined from ultrasound backscatter from the femoral head and/or neck, can be entered into the arrangement by means of the elements 306.

The arrangement comprises preferably also control elements 308 for controlling said measurement signal transmission means and reception means, such as, for example, for controlling the operation of the ultrasound transmitter 302 and receiver 304 or the X-radiation source 302 and receiver 304, such as, for example, for timing the operation of the transmission means' transmission and the reception means' operation. The control elements 308 may preferably control the operation of the transmission means 302 and/or the reception means 304 through the intermediary of the control electronics 302a, 304a associated therewith.

The arrangement comprises also processing elements 310, which are adapted to determine an estimate for the mineral density regarding a first bone of the patient by using at least said first and second parameters. According to one embodiment, the processing elements 310 may also be adapted to use at least one of the second parameters in the process of determining the estimate. The estimate is worked out preferably by means of some regression technique, such as for example by means of linear regression.

According to one embodiment, the processing elements 310 are adapted to determine a first parameter, which is related to a property change in a measurement signal launched towards some second bone of said patient which is other than the first bone after the measurement signal has been in interaction with said second bone. According to one embodiment, the processing elements 310 are adapted to determine some other parameter or quantity from a property change of the measurement signal, such as for example the thickness of tibial or ulnar/radius cortical bone from one or several points thereof, and to use this as said first parameter.

In addition, according to one embodiment, the arrangement's processing elements 310 may be adapted to conduct a correction of parameters, such as for example a correction regarding a property change in a measurement signal after the signal has been in interaction with an object of measurement, or a correction regarding the strength (dB) of ultrasound backscatter from the femoral head and/or neck with the effect of soft tissue. The correction may be based for example on DFUS technique and/or on taking into account the attenuation taking place in the cortical bone layer.

Still furthermore, according to one embodiment, the arrangement's processing elements 310 can be adapted to determine a parameter representing the degree of a patient's osteoporosis by using a mineral density estimate related to a first bone of the patient and by comparing said mineral density estimate to reference values regarded as normal in a manner described elsewhere in this document.

According to one embodiment of the present invention, the arrangement may also comprise elements 312 for determining a femoral geometric parameter (such as cross-sectional area or diameter) from the femoral shaft and/or neck as one of the second parameters, such as for example ultrasound transceiver elements and software for interpreting the received ultrasound signal and calculating the surface area, as well as elements 314 for determining a property change in an ultrasound signal launched towards said first bone after said ultrasound signal has been in interaction with said first bone, such as, for example, for determining an AIB parameter (dB) from ultrasound backscatter from the femoral head and/or neck, and elements 316 for determining a hand grip strength of the patient and using said information as one of the second parameters.

According to one embodiment of the present invention, at least some of the arrangement's elements and, especially, some of the functionalities of its processing elements 310, can be implemented programmatically for example by means of a computer program product capable of being run in the arrangement's data processing processor. In addition, according to one embodiment, said computer program can be adapted to determine an assessment of probability for bone fractures over the next 10 years, whereby, for example, the treatment guidelines for osteoporosis can be determined readily, quickly and precisely without an expensive separate measurement for example with a DXA apparatus. According to one embodiment, the computer software can be supplied for example with simple answers (yes or no) to some questions regarding fracture risk factors, after which the software is adapted to determine a probability for fracture and, according to one embodiment, to provide a guideline for the treatment, such as for example "no medication" or "measure mineral density" or "medicate".

According to one embodiment of the present invention, a computer program product for the assessment of mineral density related to a patient's first bone, wherein said first bone is associated with the femoral head, neck and/or the lumbar spine, is adapted:

to determine a first parameter, which is related to a property change in a measurement signal launched towards some second bone of the patient other than the first bone after the measurement signal has been in interaction with said second bone, and to determine an estimate for mineral density related to said patient's first bone by using said first parameter, as said computer program product is run with a data processing processor.

In addition, according to one embodiment of the present invention, the computer program product can be adapted to determine an estimate by using also a set of second parameters, which comprises at least one of the following: the patient's age, weight, height, body mass index femoral geometric parameter, such as for example cross-sectional area or diameter for example from the femoral shaft and/or neck, a property change in an ultrasound signal launched towards said first bone after said ultrasound signal has been in interaction with said first bone, such as for example an AIB parameter (dB) determined from ultrasound backscatter from the femoral head and/or neck, and the patient's hand grip strength.

Presented above are just a few embodiments for a solution of the present invention. The principle according to the present invention can naturally be modified within the scope of protection as defined by the claims, regarding for example implementation details as well as other fields of use.

The invention claimed is:

1. A method for an assessment of mineral density related to a first bone of a patient, wherein said first bone is associated with a femoral head, a femoral neck or a lumbar spine, the method comprising: —providing an ultrasonic transmitter in communication with a receiver; —determining with a pulse echo method a thickness of a cortical bone of a tubular bone, wherein said thickness is determined by a property change in a measurement signal launched by the ultrasonic transmitter towards said cortical bone of said tubular bone of the patient after the measurement signal has been in interaction with said cortical bone of said tubular bone and received by the receiver, using the measurement signal as reflected from first and second edges of said cortical bone, and said cortical bone of said tubular bone is some second bone other than said first bone, —determining a set of parameters, including an age and weight of said patient; and—combining said thickness of the cortical bone of the tubular bone and said set of parameters including said age and said weight of said patient by an equation determined by a regression technique for determination of an estimate for mineral density related to said first bone by using the equation: BMD estimate=$a-b(age)^x+c(weight)^y+d(Cth)^z$, wherein a, b, c, d, x, y, and z are constants.

2. A method according to claim 1, wherein said measurement signal is an ultrasound signal, and wherein said property change in the measurement signal is ultrasound attenuation in cortical bone, scatter, time delay, and/or velocity as reflected from the first and second edges of a tubular bone's cortical bone.

3. A method according to claim 1, wherein said tubular bone comprises at least one of the flowing: tibia, finger, and ulna, radius.

4. A method according to claim 1, wherein the thickness is a thickness of a tibial or a radius/ulnar cortical bone.

5. A method according to claim 1, wherein the determination of an estimate is conducted by additionally using the set of parameters, which further comprises at least one of the following: the patients height, body mass index, hormonal status, femoral geometric parameter of either cross sectional area or diameter from the femoral shaft and/or neck, a property change in an ultrasound signal launched towards said first bone after said ultrasound signal has been in interaction with said first bone, wherein the property change is one of the group consisting of an AIB parameter (dB) determined from ultrasound backscatter from the femoral head and/or neck, and patient's hand grip strength.

6. An arrangement for an assessment of mineral density related to a patient's first bone, wherein said first bone is associated with a femoral head, a femora neck or a lumbar spine, the arrangement comprising: —an ultrasound transmitter for transmitting with a pulse echo method an ultrasonic measurement signal towards the cortical bone of a patients tubular bone, and a receiver to receive said ultrasonic measurement signal after its interaction with a tubular bone's cortical bone, wherein said tubular bone's cortical bone is some second bone other than said first bone; —a data processing processor to compute a thickness of the cortical bone of the tubular bone by determining a property change in said ultrasonic measurement signal after the measurement signal has been in interaction with said tubular bone's cortical bone, using the measurement signal as reflected from first and second edges of the cortical bone, —a set of parameters, wherein said set of parameters comprises age and weight of said patient; and—a data processing processor to calculate an estimate for mineral density related to said patient's first bone by combining said thickness of the cortical bone of the tubular bone and said set of parameters including said age and said weight of said patient by an equation determined by a regression technique by using an equation: BMD estimate=$a-b(age)^x+c(weight)^y+d(Cth)^z$, wherein a, b, c, d, x, y, and z are constants.

7. An arrangement according to claim 6, wherein the arrangement comprises an ultrasound transmitter and receiver for generating, transmitting and receiving an ultrasonic measurement signal with a pulse echo method, and wherein said property change in the measurement signal is ultrasound attenuation in cortical bone, scatter, time delay, or velocity as reflected from the first and second edges of a tubular bone's cortical bone.

8. An arrangement according to claim 6, wherein the set of parameters additionally comprises at least one of the flowing: the patient's height, body mass index, hormonal status, femoral geometric, a property change in an ultrasound signal launched towards said first bone after said ultrasound signal has been in interaction with said first bone, wherein the property change is one of the group consisting of an AIB parameter (dB) determined from ultrasound backscatter from the femoral head and/or neck, and patients hand grip strength.

9. A method according to claim 1, wherein the determination of an estimate is conducted by additionally using the set of parameters, which further comprises at least one of the following: the patient's height, body mass index, hormonal status, femoral cross-sectional area or diameter from the femoral shaft and/or next, a property change in an AIB parameter (dB) determined from ultrasound backscatter from the femoral head and/or neck, and the patient's hand grip strength.

10. An arrangement according to claim 6, wherein the arrangement determines an estimate by additionally using he set of parameters, which further comprises at least one of the following: the patient's height, body mass index, hormonal status, cross-sectional area of diameter form the femoral shaft and/or next, a property change in an ultrasound signal launched towards said first bone after said ultrasound signal has been in interacting with said first bone, and the patient's hand grip strength.

11. A method according to claim 1, wherein the thickness is of tibial or radius/ulnar cortical bone.

12. An arrangement according to claim 6, wherein the arrangement is for determining the thickness of the cortical bone at several points.

* * * * *